(12) United States Patent
Paes et al.

(10) Patent No.: US 6,905,512 B2
(45) Date of Patent: Jun. 14, 2005

(54) SYSTEM FOR STABILIZING THE VERTEBRAL COLUMN INCLUDING DEPLOYMENT INSTRUMENTS AND VARIABLE EXPANSION INSERTS THEREFORE

(75) Inventors: Newton Paes, Sao Paolo (BR); Vera Paes, Sao Paolo (BR)

(73) Assignee: Phoenix Biomedical Corporation, Norristown, PA (US)

( * ) Notice: Subject to any disclaimer, the term of this patent is extended or adjusted under 35 U.S.C. 154(b) by 99 days.

(21) Appl. No.: 10/174,362

(22) Filed: Jun. 17, 2002

(65) Prior Publication Data

US 2002/0151977 A1 Oct. 17, 2002

Related U.S. Application Data

(62) Division of application No. 09/348,612, filed on Jul. 6, 1999, now Pat. No. 6,436,142.

(30) Foreign Application Priority Data

Dec. 14, 1998 (BR) .............................................. 9805340

(51) Int. Cl.⁷ .................................................. A61F 2/44
(52) U.S. Cl. .................................. 623/17.11; 623/17.16
(58) Field of Search .......................... 623/17.11, 17.16; 606/61

(56) References Cited

U.S. PATENT DOCUMENTS

| | | |
|---|---|---|
| 4,863,476 A | 9/1989 | Shepperd |
| 5,055,104 A | 10/1991 | Ray |
| 5,591,235 A | 1/1997 | Kuslich |
| 5,653,761 A | 8/1997 | Pisharodi |
| 5,653,762 A | 8/1997 | Pisharodi |

(Continued)

FOREIGN PATENT DOCUMENTS

| | | |
|---|---|---|
| DE | 44 16 605 C1 | 6/1995 |
| DE | 196 34 698 C1 | 4/1998 |
| EP | 0 599 766 A1 | 6/1994 |
| EP | 0 635 246 A1 | 1/1995 |
| ES | 2 099 008 A1 | 5/1997 |
| RU | 2063730 C1 | 7/1996 |
| WO | WO 90/00037 | 1/1990 |
| WO | WO 95/31158 | 11/1995 |
| WO | WO 96/27348 | 9/1996 |
| WO | WO 97/06753 | 2/1997 |
| WO | WO 98/10722 | 3/1998 |
| WO | WO 98/48738 | 11/1998 |

OTHER PUBLICATIONS

Surgical Dynamics, Inc., "Ray Threaded Fusion Cage", 1997 Brochure.

Primary Examiner—Brian E Pellegrino
(74) Attorney, Agent, or Firm—Caesar, Rivise, Bernstein, Cohen & Pokotilow, Ltd.

(57) ABSTRACT

A system is provided for stabilizing adjacent vertebra without excision of bone or resection of ligaments comprising an expansion device and a deployment system which includes a hollow expandable insert and an expansion insert. The expandable insert includes a cylindrical body having a pair of slots having a threaded outer surface. The expandable insert is located with the slots oriented perpendicular to the vertebral column between the vertebrae. The thread cuts into the cortical bone contiguous to the intervertebral space but not substantially into the cancellous bone. The expandable insert is internally threaded. The expansion insert is externally threaded and arranged to be screwed into a bore in the expandable insert by the deployment system, whereupon the slots open to spread the vertebrae apart. The deployment system includes a tool having projecting fingers located within the slots to enable the expandable insert to be screwed into the intervertebral space.

8 Claims, 4 Drawing Sheets

U.S. PATENT DOCUMENTS

| | | |
|---|---|---|
| 5,653,763 A | 8/1997 | Errico et al. |
| 5,693,100 A | 12/1997 | Pisharodi |
| 5,713,904 A | 2/1998 | Errico et al. |
| 5,716,415 A | 2/1998 | Steffee |
| 5,782,832 A | 7/1998 | Larsen et al. |
| 5,865,847 A | 2/1999 | Kohrs et al. |
| 5,865,848 A | 2/1999 | Baker |
| 6,117,174 A | 9/2000 | Nolan |
| 6,174,311 B1 * | 1/2001 | Branch et al. ............ 606/61 |

* cited by examiner

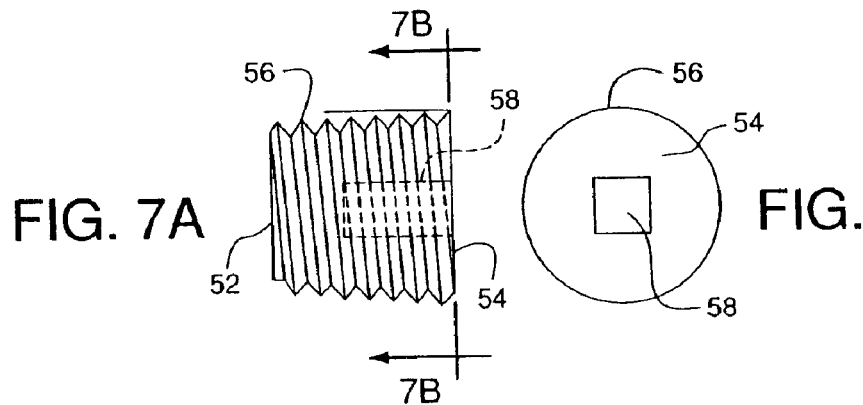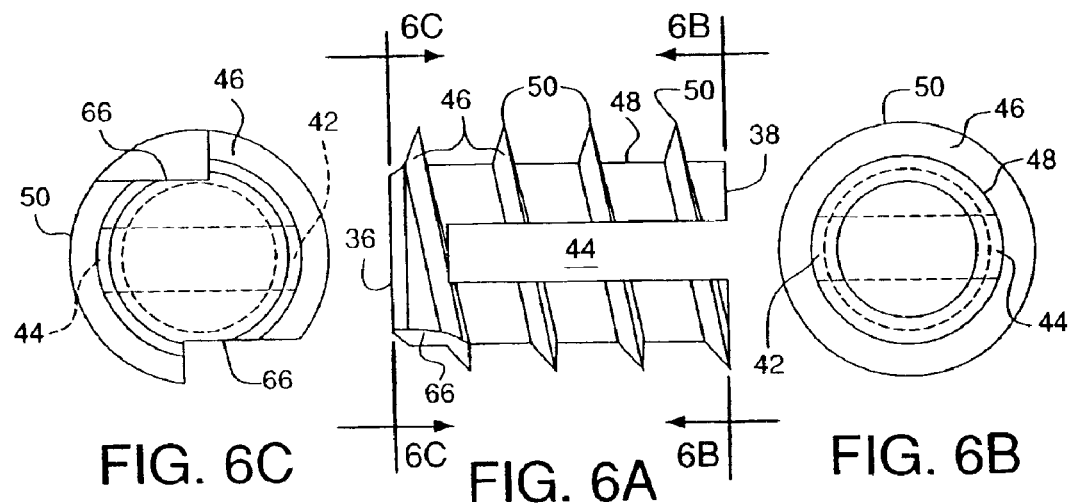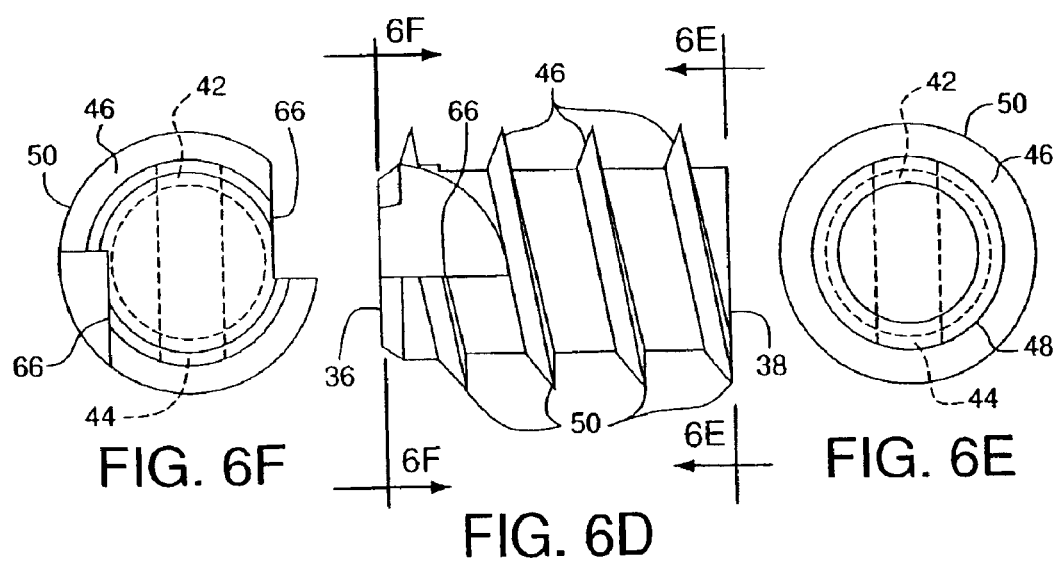

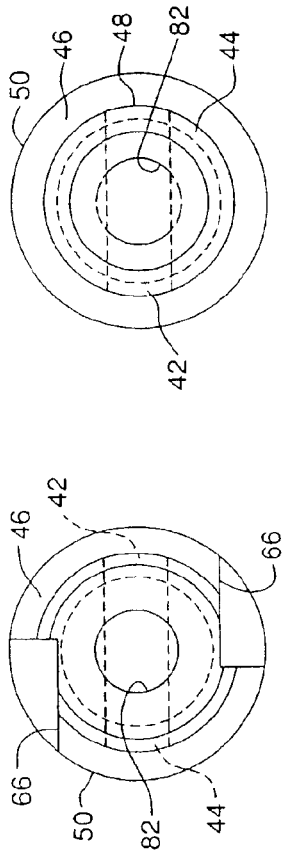
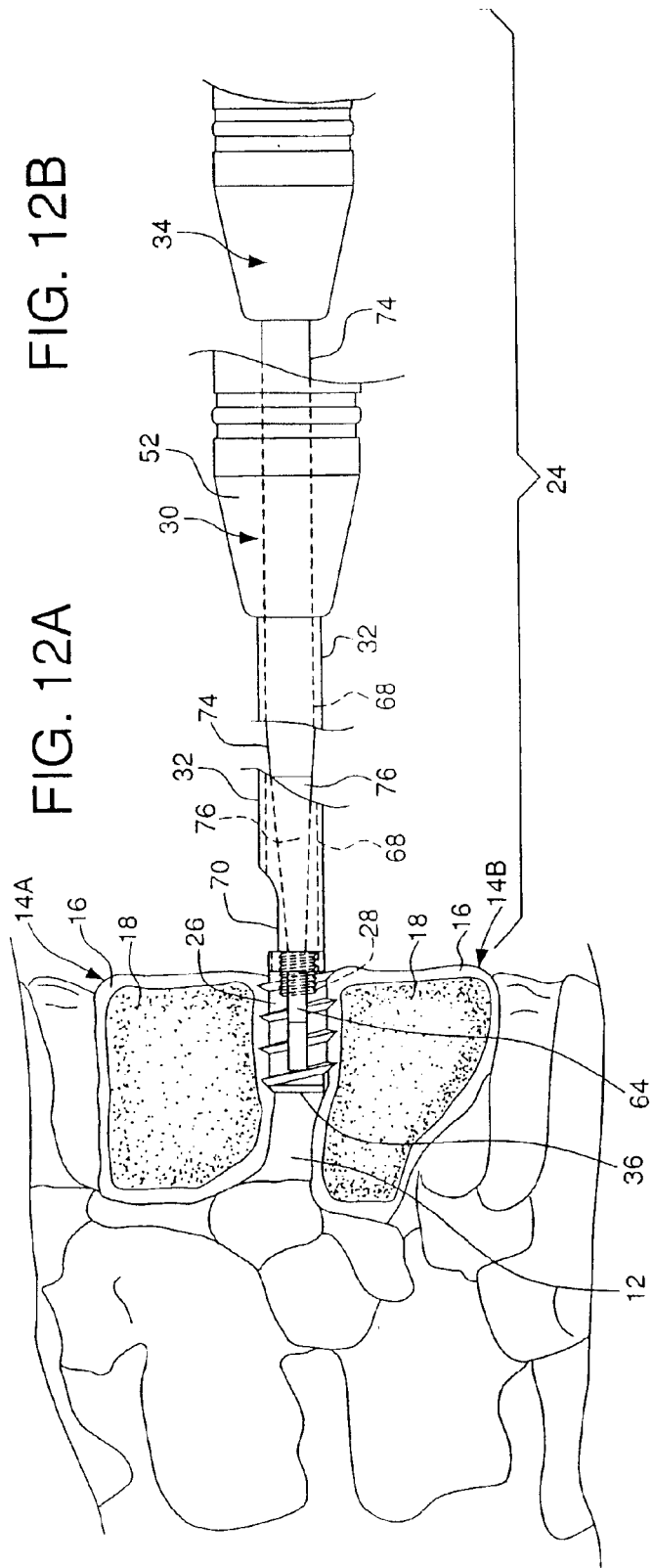
FIG. 12A
FIG. 12B
FIG. 9

SYSTEM FOR STABILIZING THE VERTEBRAL COLUMN INCLUDING DEPLOYMENT INSTRUMENTS AND VARIABLE EXPANSION INSERTS THEREFORE

CROSS-REFERENCE TO RELATED APPLICATION

This is a Divisional application of application Ser. No. 09/348,612, filed on Jul. 6, 1999, now U.S. Pat. No. 6,436,142 entitled System for Stabilizing the Vertebral Column Including Deployment Instruments and Variable Expansion Inserts Therefor.

FIELD OF THE INVENTION

This invention relates generally to medical devices and more specifically to intervertebral disk stabilization systems and methods of stabilizing the spine of living beings.

BACKGROUND OF THE INVENTION

This application claims priority on Brazilian Patent Application, Serial Number 9805340-0, filed on Dec. 14, 1998, entitled VARIABLE EXPANSION INSERT FOR STABILIZING THE VERTEBRAL COLUMN, whose disclosure is incorporated by reference herein.

Numerous types of devices or systems are available for the fixation of the vertebral column of living beings. For example, some devices are prostheses, e.g., plates or other structures, formed of rigid materials of fixed sizes and volumes capable of being fastened, e.g., bolted, to the bony structure of vertebral column anteriorly and/or posteriorly through bores excavated in those vertebrae involved. The fasteners used in such devices or systems are commonly referred to as cortical bolts or medullary bolts, depending upon the type of thread of the bolt. In some systems or devices parts of human bone from the patient himself/herself, or from bone banks or dehydrated human bone is used to aid in securing the prosthesis to the bony structure(s) of the vertebrae. One of the greatest drawbacks of such prior art devices or systems are that they are difficult to use. In this regard, the deployment and mounting of a bolt-based fixation device is delayed by the necessity to bore the bony structures of the vertebrae for receipt of the securement bolts. Moreover, the location of the bore holes for those bolts must be precisely located and oriented to match up with the pre-established holes in the plates or other support structures forming the remainder of the device or system. Another drawback of such spine fixation devices is the fact that they typically take up such substantial space in the body when secured in place, that they may result in the formation of traumatic lesions to adjacent anatomic structures. Lastly, traction exerted by movement of the patient, may cause partial or total detachment of one or more of the bone fixation bolts, which action may also result in the formation of traumatic lesions to adjacent anatomic structures and/or instability of part or all of the fixation system.

Various patents and printed patent literature have also disclosed devices and systems for fixation or stabilization of the spine or vertebral column of a living being. See for example, U.S. Pat. No.: 4,863,476 (Shepperd), U.S. Pat. No. 5,591,235 (EKuslich), U.S. Pat. No. 5,653,761 (Pisharodi), U.S. Pat. No. 5,653,762 (Pisharodi), U.S. Pat. No. 5,653,763 (Errico et al.), U.S. Pat. No. 5,693,100 (Pisharodi), U.S. Pat. No. 5,713,904 (Errico et al.), U.S. Pat. No. 5,782,832 (Larsen et al.), U.S. Pat. No. 5,865,847 (Kohrs et al.) and U.S. Pat. No. 5,865,848 (Baker), PCT Application Publication Nos.: WO 90/00037, WO 95/31158, WO 97/06753, and WO 98/10722, European Patent Application Nos.: 0 599 766 A1, and 0 635 246 A1, Spanish Patent No. ES 2 099 008, and Russian Patent No.: 2063730.

While the spine stabilization or fixation devices of the patent literature may be generally suitable for their intended purposes, they still leave much to be desired from the standpoints of ease of use and effectiveness. For example, some prior art spine fixation devices require excision of the anterior and/or posterior ligaments, thereby destabilizing the spine. Thus, these systems require some mechanical means to fuse or fix the adjacent vertebrae to each other, e.g., removal or drilling of the bone to secure the device in position with respect to each vertebra with some type of mechanical bridge therebetween. Other types of fixation devices make use of hollow or apertured implants designed to be packed with bone chips or particles and placed into excavations through the exterior, hard cortical bone, into the soft interior cancellous bone of opposed vertebrae to facilitate the ingrowth of bone into the implant and thus fuse the two vertebrae together. This type of fixation device may be prone to damage the immediately adjacent vertebrae due to compressive forces thereon.

While some prior art devices don't require excision of the ligaments to effect spine stabilization, they, nevertheless, typically require the partial or complete extraction and removal of the disk in order to place them into the intervertebral space, where such devices seek to replace the function of the disk (albeit less than optimally).

Notwithstanding all of the prior art now in existence, a need still exists for a spine stabilization system which is easy to use, effective, and safe.

OBJECTS OF THE INVENTION

It is a general object of this invention to provide a vertebral-column stabilizing device and deployment system which overcomes the disadvantages of the prior art and addresses those needs.

It is another object of this invention to provide a device and system for deploying it in the intervertebral space between a superior and inferior vertebra of a living being to stabilize the spine.

It is another object of this invention to provide a device for deployment in the intervertebral space between a superior and inferior vertebra of a living being to stabilize the spine, yet which does not require the excision of either the anterior or posterior ligament.

It is another object of this invention to provide a device and system for deploying it to stabilize the spine of a living being without requiring removal of bone.

It is another object of this invention to provide a device and system for deploying it to stabilize the spine of a living being without interruption or removal of bone growth surfaces.

It is another object of this invention to provide a device for deployment in the intervertebral space between a superior and inferior vertebra of a living being to stabilize the spine, yet which does not require the complete removal of the interposed disk, e.g., all it requires is the creation of a small opening in the disk through which the nucleus is excised.

It is another object of this invention to provide a device and system for deploying it in the intervertebral space between a superior and inferior vertebra of a living being, so that when the device is deployed it effectively stabilizes the spine.

It is another object of this invention to provide an adjustable and controllable spine stabilization device and system for deploying it in the intervertebral space between adjacent vertebra to establish a desired lordotic curvature of the spine.

It is another object of this invention to provide a spine stabilization device and system for deploying it in the intervertebral space between a superior and inferior vertebra which is easy to use.

It is another object of this invention to provide an expandable vertebral-column stabilizing device which is simple in construction.

It is another object of this invention to provide a deployment system which is simple in construction and easy to use to deploy an expandable vertebral-column stabilizing device.

SUMMARY OF THE INVENTION

A system for stabilizing the vertebral column of a living being. The system includes a variable expansion device an a deployment system for deploying the device. When deployed the device stabilizes a superior vertebra and immediately adjacent inferior vertebra of the vertebral column, without requiring the excision of bone from the superior or inferior vertebrae or the resection of the adjacent longitudinal proximal or distal ligaments.

The stabilizing device basically comprises an expandable insert and an expansion insert. The expandable insert comprises a hollow cylindrical body having a longitudinal axis, an proximal end portion and a distal end portion. The proximal end portion has a pair of slots extending therethrough generally parallel to the longitudinal axis of the expandable insert. The slots extend partially into the distal end portion of the expandable insert. The distal end portion and at least a portion of the proximal end portion of the expandable insert have an outer surface about which an external, helical, self-tapping thread extends. The distal end portion and the at least a portion of the proximal end portion of the expandable insert are of a sufficient size to be screwed into the intervertebral space between the superior and inferior vertebrae, to an operative position and orientation. In the operative position and orientation the expandable insert is located at a desired depth within the intervertebral space and its slots are oriented in a plane generally perpendicular to the portion of the longitudinal axis of the being's vertebral column between the superior and inferior vertebrae.

The self-tapping thread of the expandable insert is a sufficient height to cut into the cortical bone of the superior and inferior vertebrae contiguous to the intervertebral space, but not substantially into the cancellous bone.

The proximal end portion of the expandable insert has an internally threaded, e.g., fine threaded, bore extending through it and into and through at least a portion of the distal end portion of the expandable insert. The internally threaded bore communicates with the slots in the expandable insert.

The expansion insert has an externally threaded outer surface and is arranged to be screwed into the internally threaded bore in the proximal end portion of the expandable insert when the expandable insert is in the desired position and orientation. In a preferred embodiment the outer surface of the expansion insert is tapered from the proximal end to the distal end. Thus, when the expansion insert is screwed into the threaded bore in the expandable insert, it causes the slots to open and thereby spread the superior and inferior vertebrae apart, thereby stabilizing the being's vertebral column.

The deployment system in the preferred embodiment comprises two tools which are arranged to cooperate with each other. A first one of the tools has portion, e.g., an elongated hollow shaft having a pair of extending fingers, adapted to fit into at least one of the slots in the expansion insert to enable the tool to screw the expandable insert to the desired depth and orientation in the intervertebral space between the superior and inferior vertebrae and to hold it in the desired orientation at that depth. The second tool, e.g., an elongated rod-like shaft arranged to extend through the hollow interior of the first tool, has a working end, e.g., a square head, adapted to engage a portion, e.g., a square slot, of the expansion insert to screw the expansion into the threaded bore in the proximal end portion of the expandable insert to cause the slots to spread apart, whereupon the device stabilizes the being's vertebral column.

DESCRIPTION OF THE DRAWING

FIG. 6A is a side elevational view of the expandable insert of FIG. 1:

FIG. 6B is an end view taken along line 6B—6B of FIG. 6A;

FIG. 6C is an end view taken along line 6C—6C of FIG. 6A;

FIG. 6D is a top elevational view of the expandable insert of FIG. 6A:

FIG. 6E is an end view taken along line 6E—6E of FIG. 6D;

FIG. 6F is an end view taken along line 6F—6F of FIG. 6D;

FIG. 7A is an enlarged side elevational view of the expansion insert of FIG. 1:

FIG. 7B is an end view taken along line 7B—7B of FIG. 7A;

FIG. 9 is an illustration showing the expansion insert of FIG. 1 being inserted into the expandable insert once the expandable insert has been positioned in the intervertebral space between a superior vertebra and an inferior vertebra using the deployment tools shown in FIGS. 2, 3 and 4;

FIG. 12A is a view similar to FIG. 6C but showing an alternative expandable insert constructed in accordance with this invention to facilitate visualization of the deployment of the insert;

FIG. 12B is a view similar to FIG. 6B but showing the alternative expandable insert constructed of FIG. 12A.

DETAILED DESCRIPTION OF THE PREFERRED EMBODIMENT

Figure 1:
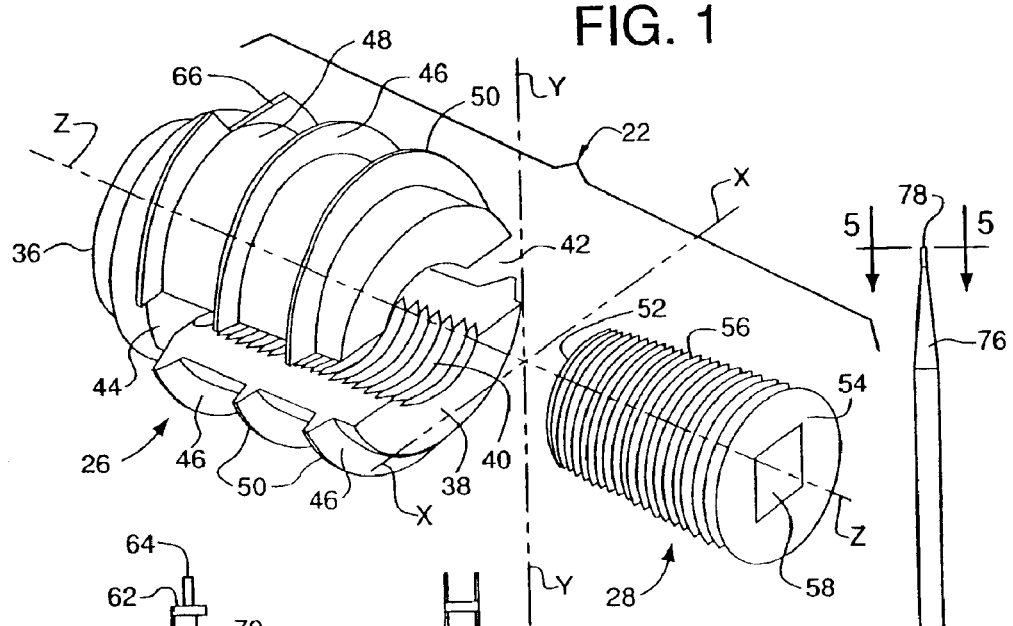
FIG. 1 is an exploded isometric view of a vertebral column stabilizing device forming a portion of a system constructed in accordance with one preferred embodiment of the invention.
Figure 3:
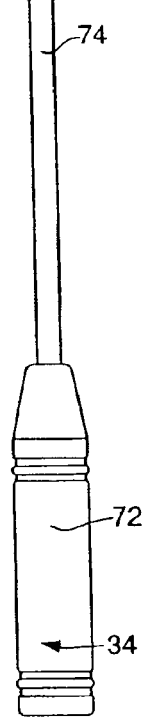
FIG. 3 is a reduced top elevational view of the tool shown in FIG. 2.

Referring now to the various figures of the drawing wherein like reference characters refer to like parts, there is shown generally at 20 in FIG. 9 a system for stabilizing the spinal column 10 of a living being. The system 20 basically comprises a stabilization device 22 and a deployment system 24 for the device. The stabilization device 22 is itself composed of two components, namely, a self-tapping expandable insert 26 and an expansion insert or screw 28 (see FIG. 1). The details of the insert 26 and expansion screw 28 will be described later. Suffice for now to say that the insert 26 is arranged to be screwed into the intervertebral space 12 between a superior vertebrae 14A and an inferior vertebrae 14B at the location to be stabilized as selected by the surgeon. Insert 26 is screwed into place by a first one of two tools making up the deployment system 24.

Once the insert 26 is in place, the expansion screw 28 is screwed into the insert 26 by the second tool of the deployment system 24. This action causes portions of the insert 26 to spread apart, whereupon the confronting portions of the inferior and superior vertebrae are concomitantly spread apart to stabilize the spinal column. The first tool of the system 24, i.e., the tool for screwing the insert into the intervertebral space 12, is designated by the reference number 30 and includes a handle 32 and an elongated hollow shaft 32. The distal free end of the tool 30 is arranged for engaging the expandable insert 26 and driving (i.e., screwing) it into the intervertebral space 12 to the desired depth and so that the insert is at an appropriate orientation (as will be described later). The second tool of the system, i.e., the tool for screwing the expansion screw 28 into the insert 26, is designated by the reference number 34. This tool is arranged to be inserted into a passageway (to be described later) in the tool 30 and to be guided thereby to carry the threaded screw 28 into the expandable insert and to screw the threaded screw to a desired depth therein. The structural details of both tools 30 and 34 will be described later.

Referring now to FIG. 1, the details of the construction of the stabilizing device 22 will now be discussed. Thus, as can be seen, the expandable insert 26 basically comprises a cylindrical member or body having a distal end 36 and a proximal end 38. A threaded, cylindrical bore 40 extends into the member from the proximal end 38 to a point close to the distal end 36. The bore is centered about the central longitudinal axis of the insert. A pair of slots 42 and 44 are cut into the sidewall of the insert at diametrically opposed locations at the proximal end of the insert and communicate with the threaded bore 40. The slots extend from the proximal end 38 to a point close to the distal end 36 and are coplanar and centered about the central longitudinal axis of the insert. A self-tapping helical thread 46 extends about the periphery of the cylindrical outer surface 48 of the expandable member. The helical thread is interrupted at each slot. The helical thread tapers from its root, i.e., the cylindrical outer surface 48 to its apex 50, to form a sharp, bone-cutting, self-tapping edge. As will be discussed later, the height (i.e., distance from the root 48 to the apex 50) of the self-tapping thread 46 is selected so that it will readily cut into the hard, cortical bone 16 of the opposed vertebrae, but not into the softer, interior cancellous bone 18.

The expandable insert 26 may be of any size consistent with the anatomy of the patient. Three particularly useful sizes are 8 mm, 9 mm and 10 mm, but such sizes are merely exemplary of any size insert which can be used. In any case, the outside diameter of the cylindrical portion 48 of the insert 26 is selected so that it will fit closely within the space between opposed vertebrae.

The expansion screw 28 basically comprises a somewhat truncated, conically shaped body having a distal end 52 and a proximal end 54. The screw tapers linearly from its larger outside diameter proximal end to its smaller outside diameter distal end. A fine helical thread 56 extends about the tapering outer surface of the screw. The threads are of the same size and pitch as those making up the threaded bore 40 in the expandable insert 26. The outside diameter of the distal end 36 of the expansion screw is just slightly less than the inside diameter of the threaded bore 40 of the expandable insert to enable the distal end of the expansion screw to be introduced into the entrance to the bore and then screwed into the bore to whatever depth is desired to cause the expansion insert to spread apart, as will be described later. The proximal end 54 of the screw includes a square slot 58 centered on the central longitudinal axis. The slot 58 extends partially into the screw and is provided to receive a comparably shaped working end of the tool 34 to screw the screw 28 into the insert 26.

It should be pointed out at this juncture that the device 22 is arranged to be screwed into the intervertebral space from either the anterior or posterior (or even lateral ) side of the spinal column, depending upon the anatomic structures to be corrected and the wishes of the surgeon. For example, for use of the system of this invention with the cervical spine it is expected that an anterior approach to that portion of the spine will be preferred, while use of the system in the lumbar spine will likely be from the posterior, although either approach (or even a lateral approach) may be accomplished in either portion of the spine. In the exemplary embodiment shown herein, the device is shown for insertion from the anterior aspect of the spinal column.

Figures 2, 4:
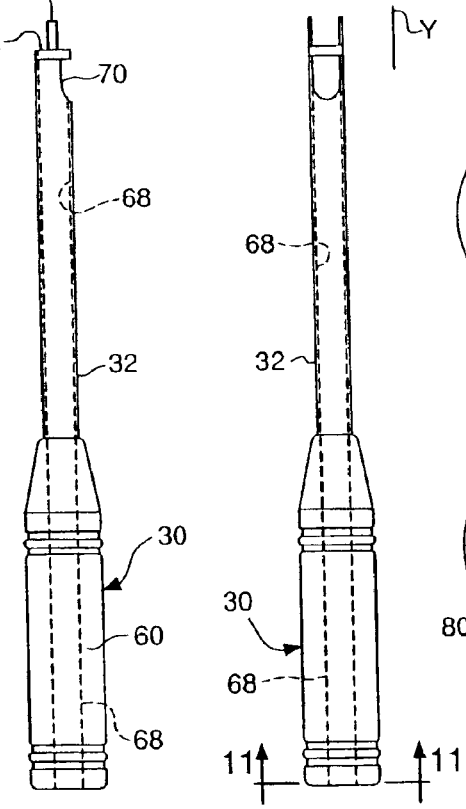
FIG. 2 is a reduced side elevational view of one tool of the system of this invention and which is arranged to insert an expandable insert forming a portion of the device shown in FIG. 1.
FIG. 4 is a reduced side elevational view of another tool of the system of this invention and which is arranged to insert an expansion insert, also forming a portion of the device of FIG. 1, into the expandable insert of FIG. 1.
Figure 5:
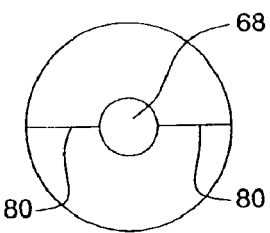
FIG. 5 is a greatly enlarged view taken along line 5—5 of FIG. 3.
Figure 11:
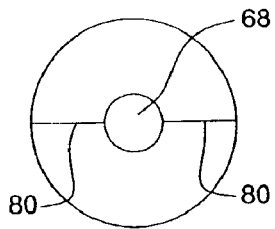
FIG. 11 is an enlarged view taken along line 11—11 of FIG. 4.
Figure 10:
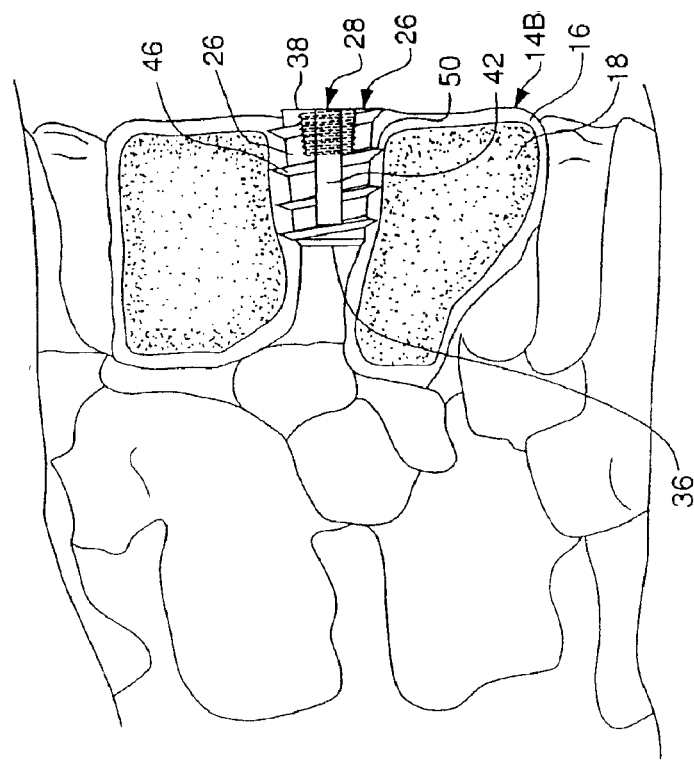
FIG. 10 is an illustration showing the stabilizing device in place after it has been deployed in the intervertebral space between a superior vertebra and an inferior vertebra to stabilize those vertebrae.
Figure 8:
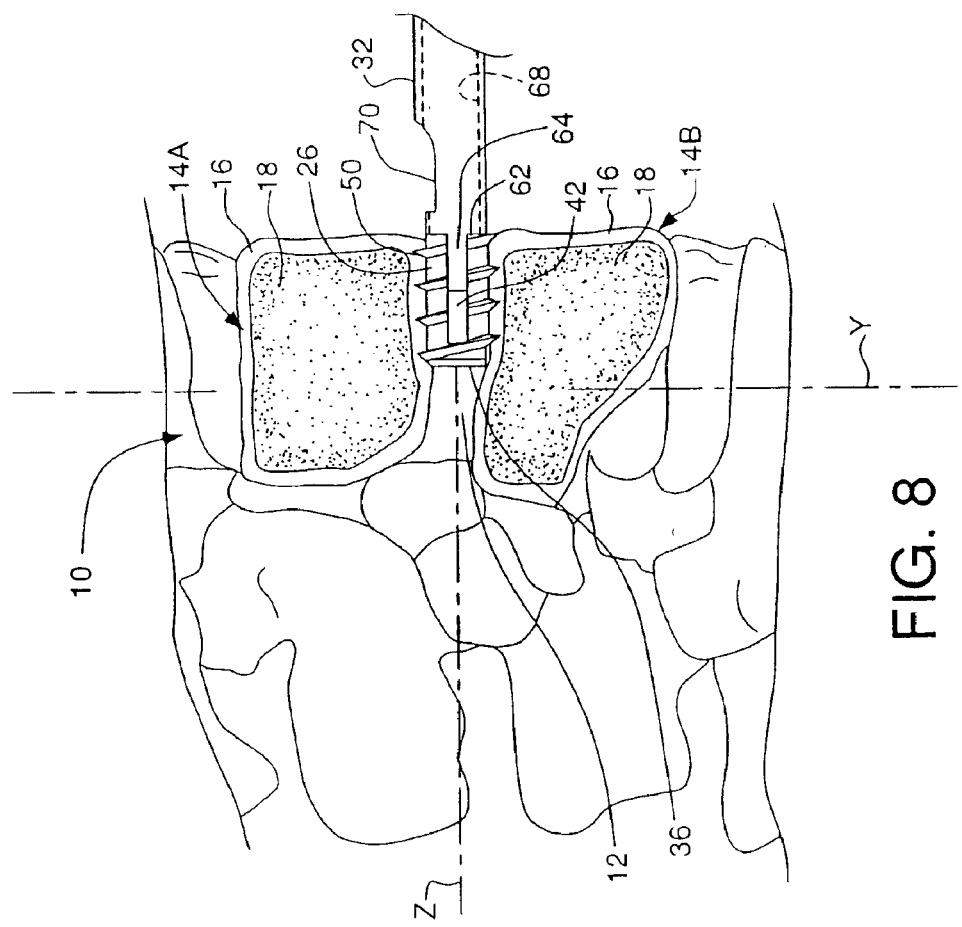
FIG. 8 is an illustration showing the expandable insert of FIG. 1 being inserted into the intervertebral space between a superior vertebra and an inferior vertebra using the deployment tool shown in FIGS. 2 and 4.

Referring now to FIGS. 2, 4 and 8, the details of the deployment tool 30 will now be described. Thus, it can be seen that the tool 30 includes a hollow handle 60 from which the heretofore identified elongated hollow shaft 32 extends. The distal end 62 of the shaft 32 terminates in a pair of opposed fingers or prongs 64. The fingers are linear members extending parallel to the longitudinal axis of the tool and are sized so that each fits into a respective one of the slots 42 and 44 in the proximal end of the expandable insert 26. This temporarily mounts the expandable insert 26 on the distal end of the tool 30. The tool can now be held by its handle 60 by the surgeon so that the distal end 36 of the insert 26 mounted thereon can be directed to face the intervertebral space 12 between the superior and inferior vertebrae, 14A and 14B, respectively. The handle 60 of the tool 30 can then be twisted in the clockwise direction while pushing inward along the longitudinal axis of the tool to cause the self-tapping threads 46 on the insert 26 to begin to cut into the hard cortical bone 16 of those vertebrae. In order to expedite the cutting action into the hard, cortical bone, a pair of sharp starter notches 66 are cut into the threads and contiguous distal end of the insert as shown in FIGS. 6A, 6C, 6D and 6F. These starter notches enable the threads 46 to readily begin to cut into the cortical bone 16 when the distal end of the expandable insert 26 is screwed into the intervertebral space 12 by the rotary force imparted by the tool 30. Continued rotation of the tool 30 about its longitudinal axis while applying inward pressure drives, i.e., screws, the insert 26 deeper into the intervertebral space 12.

When the insert is at the desired position, such as shown in FIG. 8, its slots 42 and 44 are disposed in a plane generally perpendicular to the portion of the midline axis "Y" (FIGS. 1 and 8) of the spine extending through the adjacent vertebrae 14A and 14B. In order to ensure that the slots are oriented in this plane, indicia in the form of a pair of lines 80 are provided on the end of the handle of the tool 30 for viewing by the surgeon.

With the threaded insert 26 in the desired position and orientation, such as shown in FIG. 8, it is now ready to receive the threaded screw 28. As mentioned earlier, this screw serves to spread apart portions of the insert 26. In particular, when the screw 28 is screwed into the threaded bore 40 of the insert 26, the portions of the insert body contiguous with the slots 42 and 44 spread apart to spread the contiguous vertebrae.

In accordance with the preferred embodiment of the invention shown herein, the threaded bore 40 in the expandable insert 26 is cylindrical and the threaded screw 28 is tapered, e.g., tapers at a 4° angle from its proximal end 54 to its distal end 56. As should be appreciated by those skilled in the art, alternatively, the bore 40 may be tapered and the screw 28 cylindrical. Moreover, the amount of taper between the bore and the screw can be selected to provide whatever amount of vertebral spreading is desired for any given amount of insertion of the screw within the bore. Thus, when the screw is screwed into the bore the mating flaring (tapering) and cylindrical surface threads engage each other to spread apart the portions of the expandable insert contiguous with the slots 42 and 44 as the screw is screwed deeper into the bore.

The screwing of the screw 28 into the threaded bore 40 of the insert 26 is best accomplished by first loading the screw 28 into the tool 30. To that end, as noted earlier, the tool 30 includes the hollow shaft 32 and contiguous hollow handle 60. A central passageway 68 extends down the shaft and through the handle. The inner diameter of the passageway 68 is just slightly greater than the outside diameter of the widest portion of the screw 26, i.e., its proximal end 54. Thus, the screw 28 can be inserted in the passageway 68 so that its longitudinal central axis is coaxial with the central axis of the tool 30 and with the longitudinal central axis of the expandable insert 26. The screw 28 may be introduced into the central passageway 68 of the tool 30 through either a side port or window 70 cut into the wall of the shaft adjacent the distal end 62 from which the pair of fingers 64 project. Alternatively, the screw 28 can be preloaded in the passageway 68. In either case, the screw is oriented so that its smaller diameter distal end is directed toward the free end 60 of the tool 30.

As mentioned earlier, and as shown best in FIGS. 7A and 7B, the proximal end 54 of the screw 28 includes a square slot 58 therein to receive the working end of the tool 34. While the slot in this embodiment is shown as being square, it may be of any shape to accommodate the working end of the tool 34. In a preferred embodiment of the invention, the slot 58 tapers slightly, e.g., approximately 1° from the proximal end of the slot to its bottom. Other types of slots, such as a Phillips head slot, a straight slot, a Torx head slot, etc., can be provided in the proximal end of the screw 28 to be engaged by a like shaped working end of the tool 34. The tool 34, like the tool 30, includes an elongated handle 72 and an elongated shaft 74 projecting from the handle. The distal end of the shaft 24 tapers downward at 76 to a square tip working end 78.

The outside diameter of the shaft 74 of the tool 34 is slightly less than the inside diameter of the passageway 68 in the tool 30 since the shaft is arranged to be extended through that passageway while the tool 30 holds the expandable insert 26 at the desired orientation (i.e., the slots 42 and 44 being in a plane generally perpendicular to the portion of the midline or longitudinal axis "Y" of the spinal column between the superior and inferior vertebrae). The tool 34 can then be slid further inward through the passageway 68 until its square head 78 is received within the square slot 58 in the proximal end of the screw 28 located within the passageway 68 at the distal end thereof.

Pushing inward on the screwdriver tool 34 while rotating it in the clockwise direction thus causes the screw 28 to enter into the threaded bore 40 in the insert 26. Continued rotation and inward pushing will drive the screw to the desired depth within the insert 26. All the while that the tool 34 is used to rotate the screw 28, the handle of the tool 30 is held stationary to ensure that the threaded insert 26 remains stationary (i.e., is not rotated) in its desired orientation. This feature is of considerable importance to maintain the slots 42 and 44 in the plane perpendicular to the midline axis Y of the patient's spine. In this regard, as should be appreciated by those skilled in the art, if the insert 26 were able to rotate so that its slots 42 and 44 were not disposed in that plane, the spreading action of the device 22 would effect a skewing of the adjacent vertebrae. Instead, by holding the slots so that they are in a plane perpendicular to the longitudinal axis of the spine, the system is able to provide desired vertebral spreading without skewing. In the embodiment shown, the insert 26 is oriented so that not only are the plane of its slots disposed perpendicularly to the midline axis Y, but also its longitudinal axis is coincident with the "Z" axis (an axis which as shown in FIGS. 1 and 8 extends anteriorly-posteriorly and perpendicular to the Y axis). However, this is not the only orientation that the stabilizing device 22 of this invention may be used. In particular, the insert 36 can be oriented so that its longitudinal central axis extends at some angle other than perpendicular to the transverse or "X" axis of the spinal column shown in FIG. 1, so long as the slots 42 and 44 are in a plane perpendicular to the midline (Y) axis of the spine. This feature gives the surgeon considerable leeway for the angle of the insertion approach to be taken, based on the patient's particular vertebral anatomy.

As noted earlier, the deployment of the stabilization device 22 of this invention does not require the excision or resection of either the anterior or posterior ligaments. For example, all the surgeon has to do to deploy the device 22 from the anterior aspect, such as shown in the drawings, is to merely temporarily displace the anterior ligament to the side. If necessary a small, longitudinally extending incision may be made in the ligament as an access way to the disk. This small incision should not compromise the strength of the ligament so long as it is made parallel to the longitudinal axis of the ligament. In any even, a small incision is then made into the annulus of the disk. The nucleus or a portion of the nucleus is then removed to relieve pressure on the nerve root. The annulus is left essentially intact. This provides additional support and cushioning for the vertebrae. Once the nucleus has has been removed, the device 22 can be deployed into the intervertebral space 12, such as described above. Once the device is properly deployed, the tools of the deployment system 24 can be removed, allowing the anterior ligament to assume its normal position. The tensioning of the anterior ligament, which results from the spreading of the adjacent vertebrae 14A and 14B, has the effect of stabilizing the spine.

In accordance with the proposed commercial embodiments of this invention, the expandable insert 26 and the screw 28 are each formed of wrought Titanium 6A 1-4V ELI alloy. However, this material is merely exemplary of various other kinds of strong, biocompatible materials which may be utilized in the subject invention. As mentioned earlier, the expandable insert can be made in various sizes. For example, the screw can have an outer diameter, i.e., the diameter of the exterior self-tapping threads, of 8, 9 or 10 mm. The length of the insert can also be of any desired size, e.g., 10 mm. The thickness or width of the slots is approximately 1.9 mm and the length of the slots is approximately 8.5 mm for those exemplary inserts. The root 48 of the external threads 46, i.e., the outside diameter of the cylindrical body, is approximately 6 mm for the 8 mm size insert, 7 mm for the 9 mm size insert, and 8 mm for the 10 mm size insert. All of the inserts have the same self-tapping thread 46 pitch, namely, 2.75 mm. The threaded cylindrical bore is of the insert 26 of M-4 size. The expansion screw 28 is approximately 4.5 mm long. The square slot 58 in the proximal end of the screw 28 is approximately 1.4 mm and extends approximately 3.4 mm deep into the screw.

The tool 30 has an elongated shaft of approximately 4.291 inches and an outside diameter of approximately 0.32 inch. The handle is approximately 3.5 inches long and 0.75 inches in diameter. The fingers 64 at the distal end of the insert driver 30 are approximately 0.3 inches long, approximately 0.09 inches wide and taper downward approximately 1° toward their free end. The width of the arch over the window 70 at the distal end of the expandable insert driver is approximately 0.1 inches wide.

The tool 34 has an elongated shaft of approximately 7.625 inches with an outside diameter of 0.24 inches. The handle is approximately 3.5 inches long and approximately 0.75 inches in diameter. The shaft tapers downward to a square cross-sectional area of 1.4 mm to fit within the square slot 58 in the proximal end of the screw 28. The free distal end 78 of the screwdriver 34 is approximately 0.2 inches long and tapers at an angle of 1° to its terminus.

In order to facilitate visualization and access to the intervertebral space the expandable insert 26 of this invention may be provided with a small opening or access port in the distal end of the expandable insert 26. This alternative embodiment of the expandable insert is shown in FIG. 12 and is identical in construction to the embodiment of the expandable insert described heretofore, except for the inclusion of a small access opening or port 82. As can be seen the port 82 is centered on the longitudinal axis Z and in communication with the bore 40 of the insert. This opening or port can also be used to facilitate endoscopic placement of the insert 26 after removal of the nucleus of the disk. The access opening or port should be of a sufficient size to permit the passage of an endoscope therethrough without compromising the strength or integrity of the device. Use of an expandable insert with such an access opening or port is a follows. Once the expandable insert 26 is mounted on the tool 30, an endoscope (not shown), either rigid or flexible, with a diameter smaller than the inside diameter of the passageway 68 in the tool and smaller than the diameter of the access port, can inserted through the passageway and through the access port in the expandable insert. This action will permit visualization of the placement of the expandable insert into the intervertebral space so that it is at the desired depth and orientation. Rotation of the tool 30 can be readily accomplished to achieve that end while the endoscope enables the surgeon to visually monitor the deployment of the expandable insert to ensure that placement of that insert avoids contact with any sensitive structures, e.g., the nerve root. A working channel in the endoscope could be used to effectuate irrigation and aspiration, as well as providing an access portal for the introduction of small instruments, e.g., instruments used to remove any vestiges of the nucleus which may still impinge on the nerve root.

The use of an access port 82 in the expandable insert 26 enables future entry and nerve decompression, without removal of the insert. To achieve that end all that is required is to gain access to the proximal end of the in-place expansion screw 28, either surgically or endoscopically. Once that has been achieved the expansion screw may be screwed out of the bore in the insert 26 by any suitable tool, e.g., the tool 34. After the expansion screw 28 has been removed the intervertebral space may be inspected and revised (if necessary), by use of an endoscope inserted through the bore 40 and communicating access port 82 in the insert 26.

As should be appreciated from the foregoing, the stabilizing device of the subject system makes use of a simple expandable cylindrical member including a self-tapping thread on its outside surface and a simple expansion screw. The device can be placed into the intervertebral space without requiring any bone boring. Moreover, the height of the self-tapping thread on the expandable member is selected so that it cuts into the cortical bone, but not substantially into the cancellous bone. This feature makes it particularly suitable for use on children, since it should not impede bone growth. Moreover, by virtue of the fact that the expansion screw can be screwed as deeply as desired into the threaded bore enables the user to easily control and adjust the degree of expansion of the expandable member, and hence vertebral spacing.

The co-acting tools making up the deployment system are particularly suited for deploying the expandable insert to the desired depth and orientation. To that end, one of the tools also includes a passageway for the other tool to extend therethrough to screw the threaded screw into the threaded bore to the desired depth while the first tool holds the expandable insert in the desired orientation. Once the screw is at the desired position, thereby effecting the desired amount of spreading of the expandable insert, both tools may be removed, leaving the device 22 in position stabilizing the spine.

Among the salient features and advantages of the subject invention are a reduction of the time for spinal surgery due to the ease of use and the absence of the need for prior bone boring. Moreover, the device, being adjustable, enables varying amounts of equalization of the height of the vertebral bodies to be tailored to the specific needs of each patient. All of this is accomplished at any portion of the vertebral column without occupying space outside the spinal column, which action could result in pain or traumatic injury to adjacent anatomic structures. Once in place the device is very stable and resistant to displacement notwithstanding movement or traction forces exerted physiologically by the patient. The small diameter of the device 22 and the tools for deploying it render the system of this invention particularly suitable for use in minimally invasive surgical techniques. Thus, the system of the subject invention can be deployed through a relatively small, e.g., 14 French, introducer tube like that typically used for various types of minimally invasive surgical procedures. Alternatively, the device and its deployment system can be used in conventional cut-down surgical procedures. In any case, the subject system enables the stabilization of the spine, the re-establishment of physiological distance between vertebral bodies and the re-establishment of normal lordotic curve of the spinal column, without requiring fusion of the two vertebrae to each other either by means of an implant into which bone material is either applied or grows, or a device which mechanically fixes the two vertebrae to each other via plates, bars, rods, etc.

Without further elaboration the foregoing will so fully illustrate my invention that others may, by applying current or future knowledge, adopt the same for use under various conditions of service.

We claim:

1. A system for stabilizing a superior vertebra and immediately adjacent inferior vertebra of the vertebral column of a living being without requiring the excision of bone from the superior or inferior vertebrae or the resection of the adjacent longitudinal proximal or distal ligaments, said system comprising a variable expansion device and a deployment system, said variable expansion device comprising a hollow one-piece expandable insert and an expansion insert, said expandable insert comprising a one-piece cylindrical body having a longitudinal axis and a proximal end portion and a distal end portion, said proximal end portion having a pair of slots extending therethrough generally parallel to the longitudinal axis of the expandable insert, said slots forming two cantilevered body portions of said cylindrical body, said slots extending partially into said distal end portion, said distal end portion and at least a portion of said proximal end portion of said expandable insert having an outer surface about which an external helical self-tapping thread extends, said distal end portion and said at least a portion of said proximal end portion of said expandable insert being of a sufficient size to be screwed into the intervertebral space between the superior and inferior vertebrae by said deployment instrument, whereupon said expandable insert is located at a desired depth within the intervertebral space with said slots oriented in a plane generally perpendicular to the portion of the longitudinal axis of the being's vertebral column between the superior and inferior vertebrae, said self-tapping thread being of a sufficient height to cut into the cortical bone of the superior and inferior vertebrae contiguous to the intervertebral space but not substantially into the cancellous bone thereof such that said outer surface of said expandable insert about which said external thread extends does not substantially displace any cortical bone, said proximal end portion of said expandable insert having an internally threaded bore extending therethrough and into at least a portion of said distal end portion, said internally threaded bore communicating with said slots said expansion insert having an externally threaded outer surface and being arranged to be screwed into said bore in said proximal end portion of said expandable insert by said deployment system, said expansion insert having an outer diameter adapted to cause said cantilevered body portions to deflect outwardly when said expandable insert is in said desired depth, whereupon said slots open to spread the superior and inferior vertebrae apart, thereby stabilizing the being's vertebral column, said deployment system comprising a tool which includes a pair of projecting fingers arranged to be located within respective ones of said slots to enable said expandable insert to be screwed into the intervertebral space to said desired depth.

2. The system of claim 1 wherein said tool includes indicia thereon for indicating when said expandable insert is in said desired depth within the intervertebral space.

3. The system of claim 1 wherein said fingers are arranged to be located in said slots when said expandable insert is in said desired depth to immobilize said expandable insert while said expansion insert is screwed into said bore in said expandable insert.

4. The system of claim 1 wherein said tool includes an elongated hollow distal end portion from which said arms project.

5. The system of claim 1 wherein said deployment system comprises a driver tool and wherein said expansion insert includes a proximal end having a first portion arranged to be engaged by said driver tool for screwing said expansion insert into said bore of said expandable insert.

6. The system of claim 5 wherein said first portion comprises a slot.

7. A system for stabilizing a superior vertebra and immediately adjacent inferior vertebra of the vertebral column of a living being without requiring the excision of bone from the superior or inferior vertebrae or the resection of the adjacent longitudinal proximal or distal ligaments, said system comprising a variable expansion device and a deployment system, said variable expansion device comprising a one-piece hollow expandable insert and an expansion insert, said expandable insert comprising a one-piece cylindrical body having a longitudinal axis and a proximal end portion and a distal end portion, said proximal end portion having a pair of slots extending therethrough generally parallel to the longitudinal axis of the expandable insert, said slots forming two cantilevered body portions of said cylindrical body, said slots extending partially into said distal end portion, said distal end portion and at least a portion of said proximal end portion of said expandable insert having an outer surface about which an external helical self-tapping thread extends, said distal end portion and said at least a portion of said proximal end portion of said expandable insert being of a sufficient size to be screwed into the intervertebral space between the superior and inferior vertebrae by said deployment instrument, whereupon said expandable insert is located at a desired depth within the intervertebral space with said slots oriented in a plane generally perpendicular to the portion of the longitudinal axis of the being's vertebral column between the superior and inferior vertebrae, said self-tapping thread being of a sufficient height to cut into the cortical bone of the superior and inferior vertebrae contiguous to the intervertebral space but not substantially into the cancellous bone thereof such that said outer surface of said expandable insert about which said external helical thread extends does not substantially displace any cortical bone, said proximal end portion of said expandable insert having an internally threaded bore extending therethrough and into at least a portion of said distal end portion, said internally threaded bore communicating with said slots, said expansion insert having an externally threaded outer surface and being arranged to be screwed into said bore in said proximal end portion of said expandable insert by said deployment system, said expansion insert having an outer diameter adapted to cause said cantilevered body portions to deflect outwardly when said expandable insert is in said desired depth, whereupon said slots open to spread the superior and inferior vertebrae apart, thereby stabilizing the being's vertebral column, wherein said deployment system is arranged to immobilize said expandable insert at said desired depth when said expansion insert is screwed into said bore and wherein said deployment system comprises a driver tool and wherein said expansion insert includes a proximal end having a first portion arranged to be engaged by said driver tool.

8. The system of claim 7 wherein said deployment system comprises a first tool having an elongated hollow distal end portion from which a pair of fingers project, said projecting fingers being arranged to be located within respective ones of said slots to enable said expandable insert to be screwed into the intervertebral space to said desired depth and for holding said expandable insert immobilized at said desired depth, said driver tool being arranged for location within said hollow distal end portion of said first tool for screwing said expansion insert into said bore of said expandable insert when said expandable insert is immobilized at said desired depth.

* * * * *